US009896398B2

(12) United States Patent  
Porter et al.

(10) Patent No.: US 9,896,398 B2
(45) Date of Patent: Feb. 20, 2018

(54) XYLENE SEPARATION PROCESS AND APPARATUS

(71) Applicant: ExxonMobil Chemical Patents Inc., Baytown, TX (US)

(72) Inventors: John R. Porter, Lake City, MI (US); Timothy P. Bender, Houston, TX (US); Dana L. Pilliod, League City, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 8 days.

(21) Appl. No.: 15/262,648

(22) Filed: Sep. 12, 2016

(65) Prior Publication Data
US 2017/0036973 A1 Feb. 9, 2017

(51) Int. Cl.
C07C 7/12 (2006.01)
B01D 15/18 (2006.01)

(52) U.S. Cl.
CPC ............ *C07C 7/12* (2013.01); *B01D 15/1807* (2013.01); *B01D 15/1828* (2013.01); *B01D 15/1835* (2013.01); *B01D 15/1842* (2013.01)

(58) Field of Classification Search
None
See application file for complete search history.

(56) References Cited

U.S. PATENT DOCUMENTS

| 3,040,777 | A | 6/1962 | Carson et al. |
| 3,201,491 | A | 8/1965 | Stine et al. |
| 3,422,848 | A | 1/1969 | Liebman et al. |
| 3,706,812 | A | 12/1972 | Derosset et al. |
| 3,761,533 | A | 9/1973 | Otani et al. |
| 4,006,197 | A | 2/1977 | Bieser |
| 4,029,717 | A | 6/1977 | Healy et al. |
| 4,031,156 | A | 6/1977 | Geissler et al. |
| 4,992,618 | A | 2/1991 | Kulprathipanja |
| 5,750,820 | A | 5/1998 | Wei |
| 5,884,777 | A | 3/1999 | Pan et al. |
| 6,017,448 | A | 1/2000 | Hotier et al. |
| 6,110,364 | A | 8/2000 | Hotier et al. |
| 6,149,874 | A | 11/2000 | Hotier |
| 7,396,973 | B1 | 7/2008 | Winter |
| 7,582,207 | B2 | 9/2009 | Hotier et al. |
| 7,649,124 | B2 * | 1/2010 | Lee ............... B01D 15/1842 422/139 |
| 7,977,526 | B2 | 7/2011 | Porter |
| 8,008,536 | B2 | 8/2011 | Winter et al. |
| 8,168,845 | B2 | 5/2012 | Porter et al. |
| 8,481,798 | B2 | 7/2013 | Schaefer et al. |

(Continued)

FOREIGN PATENT DOCUMENTS

WO WO95/07740 3/1995

*Primary Examiner* — Tam M Nguyen (57) ABSTRACT

A simulated moving bed process using dual, parallel rotary valves configured or plumbed to be operated independently in which the step times of the rotary valves are staggered. In embodiments, the second rotary valve is programmed to step about halfway through the step time of the first rotary valve. Staggering the step time of the parallel rotary valves, rather than utilizing simultaneous stepping, results in increased net composite paraxylene concentration of the extract stream, allowing for increased capacity of the simulated moving bed process and/or reduced energy consumption.

7 Claims, 4 Drawing Sheets

(56) References Cited

U.S. PATENT DOCUMENTS

| | | |
|---|---|---|
| 8,529,757 B2 | 9/2013 | Go et al. |
| 8,569,564 B2 | 10/2013 | Porter et al. |
| 8,580,120 B2 | 11/2013 | Porter |
| 8,802,913 B2 | 8/2014 | Porter |
| 2006/0199989 A1 | 9/2006 | Frey |
| 2007/0149841 A1* | 6/2007 | Lee ..................... B01D 15/185 585/826 |
| 2008/0149565 A1* | 6/2008 | Lee .................... B01D 15/1842 210/663 |
| 2009/0036726 A1 | 2/2009 | Leflaive et al. |
| 2010/0125163 A1* | 5/2010 | Porter ................ B01D 15/1835 585/822 |
| 2013/0158335 A1* | 6/2013 | Corradi .................... C07C 7/12 585/828 |
| 2015/0005561 A1* | 1/2015 | Pieper .................... C07C 7/005 585/802 |
| 2015/0087876 A1* | 3/2015 | Sanger ..................... C07C 7/12 585/805 |

* cited by examiner

XYLENE SEPARATION PROCESS AND APPARATUS

CROSS REFERENCE TO RELATED APPLICATIONS

This application is a Divisional Application of U.S. Ser. No. 14/885,319, filed Oct. 16, 2015, now U.S. Pat. No. 9,464,012 which claims priority to and the benefit of U.S. Provisional Application No. 62/082,238, filed Nov. 20, 2014, both of which are incorporated herein by reference in their entirety.

FIELD OF THE INVENTION

The invention relates to an adsorption apparatus and process and more particularly to a process for producing high-purity para-xylene.

BACKGROUND OF THE INVENTION

Continuous separation processes for the selective adsorption of para-xylene from a mixture of other xylene isomers, ethylbenzene, and non-aromatic hydrocarbons are common in industry. Generally, the processes use a solid adsorbent which preferentially retains the para-xylene in order to separate the para-xylene from the rest of the mixture. Often, the solid adsorbent is in the form of a simulated moving bed, where the bed of solid adsorbent is held stationary, and the locations at which the various streams enter and leave the bed are periodically moved. The adsorbent bed itself is usually a succession of fixed sub-beds. The shift in the locations of liquid input and output in the direction of the fluid flow through the bed simulates the movement of the solid adsorbent in the opposite direction. In one commercial embodiment of a simulated moving bed adsorption apparatus, the Parex™ process, moving the locations of liquid input and output is accomplished by a fluid directing device known generally as a rotary valve which works in conjunction with distributors located between the adsorbent sub-beds. The rotary valve accomplishes moving the input and output locations through first directing the liquid introduction or withdrawal lines to specific distributors located between the adsorbent sub-beds. After a specified time period, called the step time, the rotary valve advances one index and redirects the liquid inputs and outputs to the distributors immediately adjacent and downstream of the previously used distributors. Each advancement of the rotary valve to a new valve position is generally called a valve step, and the completion of all the valve steps is called a valve cycle. The step time is uniform for each valve step in a valve cycle, and is generally from about 60 to about 120 seconds, such as 90 seconds. A typical process contains 24 adsorbent sub-beds, 24 distributors located between the 24 adsorbent sub-beds, two liquid input lines, two liquid output lines, and associated flush lines.

Figure 1:
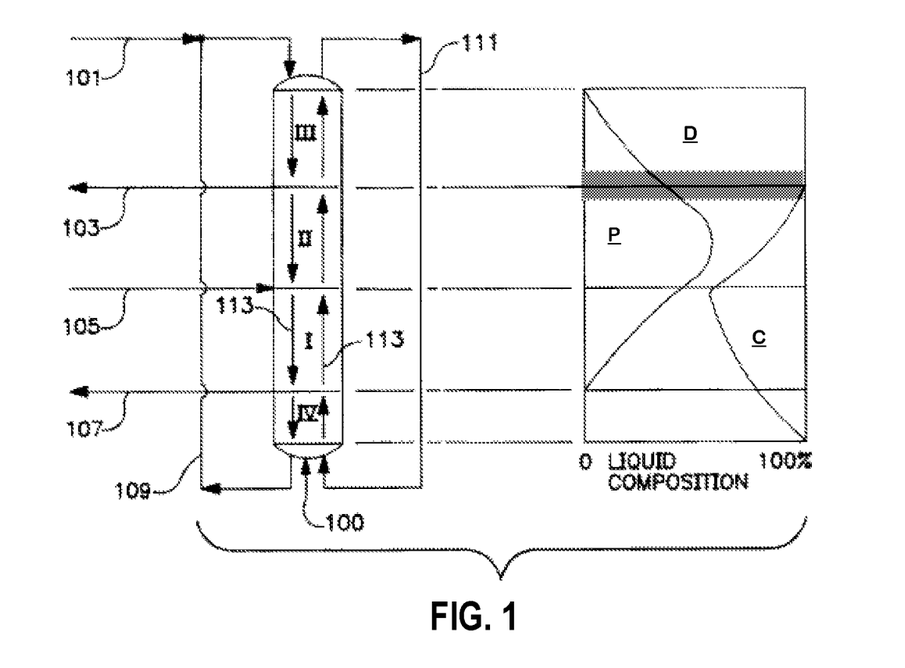
FIG. 1 is a combined flow diagram and composition chart which illustrates the relative flows and compositions of adsorbent solids and fluids in a simulated moving bed adsorption process.

The principal liquid inputs and outputs of the adsorbent system consist of four streams: the feed, the extract, the raffinate, and the desorbent. Each stream flows into or out of the adsorbent system at a particular flow rate, and each flow rate is independently controlled. With reference to FIG. 1, the feed, which is introduced to the adsorbent system 100 through fluid communication conduit 105, contains the para-xylene (PX), represented as P in the composition chart, which is to be separated from other components in the feed stream, which typically include ethylbenzene (EB), metaxylene (MX), orthoxylene (OX), toluene, various C9+ aromatics, and non-aromatics, collectively represented as C in the composition chart. The desorbent, represented as D in the composition chart, which contains a liquid capable of displacing feed components from the adsorbent, is introduced to the adsorbent system 100 by fluid communication conduit 101. The extract, which is withdrawn from the adsorbent system 100 by fluid communication conduit 103, contains the separated para-xylene which was selectively adsorbed by the adsorbent and desorbent liquid. The raffinate, which is withdrawn from the adsorbent system 100 by fluid communication conduit 107, contains the other xylene isomers, ethylbenzene, non-aromatic hydrocarbons which were less selectively absorbed by the adsorbent and desorbent liquid. There also may be associated flush streams introduced to and withdrawn from the adsorbent system. These flush streams can vary in composition and rate and can include but are not limited to para-xylene, ethylbenzene, metaxylene, orthoxylene, and desorbent. The flush flow rates are typically independently controlled. The four principal streams are spaced strategically throughout the adsorbent system and divide the sub-beds into four major zones, each of which performs a different function.

Referring to FIG. 1, Zone I contains the adsorbent sub-beds located between the feed input and the raffinate output, and selective adsorption of the para-xylene takes place in this zone. Zone II contains the adsorbent sub-beds located between the extract output and the feed input, and the desorption of components other than para-xylene takes place in this zone. Zone III contains the adsorbent sub-beds located between the desorbent input and the extract output, and the para-xylene is desorbed in this zone. Finally, Zone IV contains the adsorbent sub-beds located between the raffinate output and the desorbent input, and the purpose of this zone is to prevent the contamination of the para-xylene with other components. The flush flows are introduced in the sub-beds of some of the major zones and create minor zones which are a function of the major zone rates and the smaller flush flow rates. The graph in FIG. 1 is a fluid composition chart showing the dynamics of the relative percentages of the three components (P-para-xylene, C-other feed components, D-desorbent) in fluid moving through the system. The composition of the fluid within the system is illustrated on a corresponding reference between system 100 and the graph. As the locations at which the various streams enter and leave the system change, the zones and corresponding composition profile move as well.

Two other important streams are the pumparound and pusharound streams. In a typical para-xylene separation process, the adsorbent bed consisting of 24 sub-beds is split into two main chambers. One chamber contains sub-beds 1 through 12 and the other contains sub-beds 13 through 24. Although functionally the adsorbent system as a whole does not have a top or a bottom, each chamber has a physical top and bottom. The pumparound and pusharound streams each conduct the liquid effluent exiting the physical bottom of one adsorbent bed chamber back up to reenter the physical top of the other adsorbent bed chamber. The pumparound stream is the stream that conducts the effluent of sub-bed 24 from the physical bottom of the second chamber to reenter sub-bed 1 at the physical top of the first chamber. The pusharound stream conducts the effluent of sub-bed 12 from the physical bottom of the first chamber to reenter sub-bed 13 at the physical top of the second chamber. It is important to note that the composition of the pumparound or pusharound stream changes with each valve step, and in one valve cycle, both streams will have sequentially carried the composition which corresponds to each valve position.

In refineries that produce large volumes of xylenes or have feedstreams with different concentrations of para-xylene, i.e., reformate, transalkylation, toluene disproportionation, selective toluene disproportionation, xylene isomerization, filtrate from a p-xylene crystallizer, and so on, a simulated moving bed process with dual rotary valves for additional feed and/or flush streams may be used. Operating the dual rotary valves independently allows for optimization of multiple feed locations and/or an increased number of flushes. Such a process is described in U.S. Pat. No. 8,168,845. However, there is an ongoing need to optimize the efficiency of the simulated moving bed process.

SUMMARY OF THE INVENTION

The invention is directed to a simulated moving bed process using dual, parallel rotary valves configured or plumbed to be operated independently in which the step times of the rotary valves are staggered. In embodiments, the second rotary valve is programmed to step at some time later than the first rotary valve. In a particular embodiment, the second rotary valve steps about halfway through the step time of the first rotary valve. Staggering the step time of the parallel rotary valves, rather than utilizing simultaneous stepping, results in increased net composite para-xylene concentration of the extract stream, allowing for increased capacity of the simulated moving bed process and/or reduced energy consumption.

These and other objects, features, and advantages will become apparent as reference is made to the following detailed description, preferred embodiments, examples, and appended claims.

DETAILED DESCRIPTION

According to the invention, the purity of para-xylene extract from a simulated moving bed process and the overall separation efficiency of the process are improved by staggering the step times of dual rotary valves. As used herein, staggering the step times means stepping a second rotary valve at a different time than a first rotary valve such that the dual rotary valves do not step simultaneously. While the number of steps in the process doubles by staggering the step times of the dual rotary valves, the degree of difference in para-xylene concentration in the extract between the start of the step time and the end of the step time lessens, resulting in improved net composite para-xylene concentration.

Various terms used in this description will be understood in the context of this description. A further explanation of certain terms used herein is provided below.

C8 aromatics are aromatic compounds having 8 carbon atoms. Examples of C8 aromatics include para-xylene, metaxylene, orthoxylene, and ethylbenzene.

Equilibrium xylene is a mixture of C8 aromatics having a thermodynamic equilibrium concentration of the various C8 aromatic compounds when the C8 aromatics are subjected to non-selective isomerization conditions. Equilibrium xylene may be produced in a non-selective process for producing xylenes. A non-selective process for producing xylenes may involve reacting reactants over a non-selective catalyst. Equilibrium xylene may be produced, for example, in a xylene isomerization process, a transalkylation process or a reforming process. Equilibrium xylenes may also be produced by other processes such as methanol to aromatics processes or from bio-derived feedstocks. Equilibrium xylene may comprise, for example, about 23 percent para-xylene, based on the total of the xylenes.

Enhanced para-xylene is a mixture of C8 aromatics having a greater concentration of para-xylene than equilibrium xylene. Enhanced para-xylene may be produced in a selective process for producing xylenes. A selective process for producing xylenes may involve reacting reactants over a selective catalyst. Enhanced para-xylene may be produced, for example, by a selective toluene disproportion process or a selective toluene alkylation process. Enhanced para-xylene may also be produce by other processes. Enhanced para-xylene may have a concentration of, for example, at least 75% para-xylene, based on the total of C8 aromatics.

A non-selective process for producing xylenes is a process which produces equilibrium xylenes. A non-selective process for producing xylenes may take place over a non-selective catalyst. Examples of non-selective catalysts include large pore zeolites, such as zeolite X and zeolite Y, or amorphous aluminosilicates. When toluene is disproportionated over a large pore sixe zeolite, equilibrium zeolites may be produced.

A selective process for producing para-xylene (PX) is a process which produces para-xylene in preference to other xylene isomers (MX and OX). A selective process for producing para-xylene may be produced, for example, by catalytic process over a para-xylene selective catalyst. Examples of para-xylene selective catalysts include medium pore size zeolites, such as ZSM-5, modified with selectivating agents. Selectivating agents may neutralize surface catalytic sites or narrow the pores of the catalyst. Examples of para-xylene selective catalysts and selectivating agents are provided by in U.S. Pat. No. 5,365,004, International Publication No. WO 2013/330093, and U.S. Pat. No. 4,088,706.

Circulating bulk fluid is the fluid (i.e., liquid) which flows in a continuous manner through a simulated moving bed adsorption apparatus. The concentration of compounds in this circulating bulk fluid changes as this fluid flows through the apparatus due to, inter alia, adsorption and desorption of xylenes, ethylbenzene and desorbent, withdrawal of fluids in extract and reformate streams, and introduction of fluids through feed, desorbent and flush streams.

A rotary valve device is a device comprising at least one rotary valve. The rotary valve device may comprise various control and accessory means, such as inlet lines, outlet lines and valves associated therewith. The rotary valve device may comprise a manifold arrangement of devices to cause the adsorbent solids to flow, in a simulated manner, in a countercurrent manner with respect circulating bulk fluid.

A simulated moving bed adsorption apparatus is an apparatus including beds of adsorbent stacked in at least one column. In operative use of the adsorption apparatus, the beds are connected in a fluid and circular manner in series with one another.

A simulated countercurrent adsorptive separation is a separation which takes place in a simulated moving bed adsorption apparatus.

An adsorbent column is an apparatus having adsorbent beds stacked one on top of the other.

An adsorbent bed chamber is a chamber in an adsorption apparatus containing a bed of adsorbent (i.e., adsorbent bed).

An adsorbent bed is a bed of adsorbent contained within an adsorbent bed chamber. An adsorbent column includes multiple adsorbent beds. An adsorbent apparatus has one or more adsorbent columns. Any fluid in an adsorbent bed chamber, whether or not adsorbed on an adsorbent, is considered to be part of the bed. Accordingly, when fluid is introduced into or withdrawn from an adsorbent bed chamber, the fluid is considered as being introduced or withdrawn into or from the bed itself An adsorbent is a solid material, which selectively adsorbs desorbent in preference to para-xylene and which selectively adsorbs para-xylene in preference to metaxylene, orthoxylene, and ethylbenzene. In a simulated moving bed apparatus, such as a Parex™ unit, examples of adsorbents include charcoal, ion-exchange resins, silica gel, activated carbon, zeolitic material, and the like. An adsorbent, which is particularly useful for separating para-xylene from other C8 aromatics, is a faujasite-type molecular sieve material, such as zeolite X or zeolite Y, optionally, substituted or treated with an enhancing agent, such as a Group I or II element, such as potassium or barium. Examples of adsorbents for separating para-xylene from other C8 aromatics are described in U.S. Pat. No. 3,761,533.

A desorbent is a liquid, which is equally or slightly more preferentially adsorbed on the adsorbent than para-xylene. The desorbent should have a boiling point significantly different than the boiling points of C8 aromatics, such that the desorbent may be separated from C8 aromatics by distillation. Examples of desorbents for a para-xylene separation process include paradiethylbenzene and toluene.

Unless otherwise specified herein, the terms, downstream and upstream, refer to the direction of flow of circulating bulk fluid.

A number of abbreviations are used herein. PX stands for para-xylene. MX stands for metaxylene. OX stands for orthoxylene. EB stands for ethylbenzene. pDEB stands for paradiethylbenzene. TOL stands for toluene. NA stands for non-aromatics. Non-aromatics, such as paraffins, may be introduced into an adsorption apparatus as a feed impurity, especially when the feed comprises C8 aromatics obtained from a reforming process.

Figure 2:
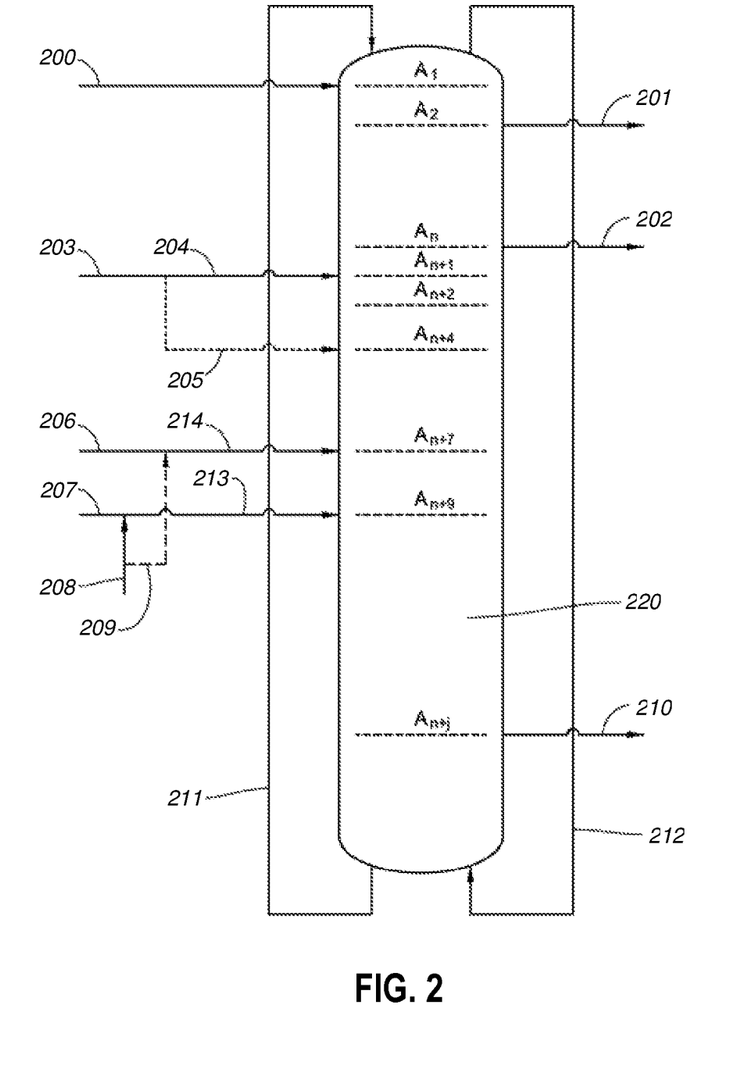
FIG. 2 is a schematic illustration of a simulated moving bed adsorptive separation system.

As described more fully in U.S. Pat. No. 8,529,757, a system employing a simulated countercurrent flow process such as described in U.S. Pat. Nos. 3,201,491; 3,761,533; and 4,029,717, are shown in FIG. 2, along with several modifications. The diagram in FIG. 2 will be understood by those of skill in the art to depict a simulated moving bed process. Desorbent is introduced through conduit 200. Liquid withdrawal stream leaves the apparatus through conduit 201. Extract (containing the desired product) leaves the apparatus via conduit 202. Raffinate leaves the apparatus through conduit 210. The secondary flush is added through conduit 203. The primary flush is added through conduit 206. A C8 aromatic feed, which comprises 15 to 30 volume percent para-xylene, is added to the apparatus through conduit 207. Optionally, a C8 aromatic mixture, which comprises 75 to 98 volume percent para-xylene, is added as an additional feed through conduit 208. Optionally, a C8 aromatic mixture, which comprises 80 to 95 volume percent para-xylene is added as a portion of the primary flushing medium through conduit 209, as explained more fully in the following description.

Not shown in the drawing, but as would be recognized by one of skill in the art in possession of the disclosure of U.S. Pat. No. 8,529,757, is one or more distillation towers and attendant pumps and conduits, which may be utilized to purify the liquid withdrawal stream leaving the above-described apparatus via conduit 201. However, such downstream operations can be minimized or entirely omitted by rerouting (such as by replumbing or retrofitting) the liquid withdrawal stream from conduit 201 to conduit 203. In this way, the liquid withdrawal stream from conduit 201 is used as the secondary flush medium, which is introduced into the apparatus through conduit 203.

Continuing with the description of FIG. 2, the arrow 212 represents the simulated movement of beds upward through apparatus 220 containing plural adsorption bed chambers $A_1$ through $A_{n+j}$. Arrow 211 represents the countercurrent flow of circulating bulk fluid to the adsorbent beds. In operation, the adsorbent does not flow, but the various inlet and outlet streams, such as feed, product and flush streams, cycle through the adsorbent bed chambers, represented by lines $A_1$ through $A_{n+j}$, in a direction, which is countercurrent to the simulated movement of adsorbent beds and concurrent to the direction of the circulating bulk fluid. This simulates the movement of the adsorbent beds $A_1$ through $A_{n+j}$. Theoretically, there may be any number of adsorbent beds, thus n>2 and n+j is the maximum number of adsorbent beds. However, from a practical standpoint, the number of bed lines is limited by design considerations and other factors. It will be understood that n and j are positive integers and that in an example of a commercial embodiment the total number of adsorbent beds is 24, and thus n+j typically may be 24. Certain adsorbent beds, i.e., beds between $A_2$ and $A_n$, beds $A_{n+3}$, $A_{n+5}$, $A_{n+6}$, and $A_{n+10}$ through $A_{n+j-1}$ are not depicted in FIG. 1, for convenience of view.

In the unit shown in FIG. 2, xylene and ethylbenzene molecules from feed 207 are adsorbed in bed $A_{n+9}$. As the adsorbent in bed $A_{n+9}$ becomes saturated with C8 aromatics, a portion of the C8 aromatics in the feed flow along with circulating bulk fluid and flow into at least one bed, such as $A_{n+10}$ (not shown in FIG. 2), below bed $A_{n+9}$. According to a predetermined cycle time, the flow of feed, along with the flows of other inlet and outlet streams, is shifted to one adsorbent bed below. In FIG. 2 the bed below $A_{n+9}$ would be bed $A_{n+10}$ (not shown in FIG. 2). The direction of the shifting of feed and other streams to and from the adsorbent apparatus is the same as the direction of the flow of the circulating bulk fluid through the apparatus. This shifting of streams results in adsorbed C8 aromatics being moved (in a simulated manner) to beds above the bed to which feed is being introduced at any given time.

The feed which is introduced through conduit 207 may comprise equilibrium xylenes (such as from a powerformer, isomerization unit or transalkylation unit). Such equilibrium xylenes may comprise about 21-24 wt % para-xylene (PX). A portion of the feed introduced through conduit 207, may also comprise enhanced para-xylene, for example, from a selective toluene disproportionation unit (STDP unit). This enhanced para-xylene may comprise, for example, about 85-90 wt % PX. In one embodiment, the feed introduced through conduit 207 is free of enhanced para-xylene from a toluene disproportional process.

The para-xylene is desorbed from adsorbent in the beds by desorbent, which is introduced into bed $A_1$ of the adsorption apparatus through conduit 200. The desorbent has a stronger binding affinity to the adsorbent than any of the C8 aromatics. The desorbent also has a different boiling point than the C8 aromatics and is easily separated from C8 aromatics in a distillation process. Examples of desorbents include paradiethylbenzene (pDEB), toluene (TOL), tetralin, or a mixture thereof, or some other strongly adsorbed compound. The stream, which is introduced into the apparatus through conduit 200, may, optionally, also comprise a diluent, such as a non-aromatic (NA) hydrocarbon, which has less binding affinity to the adsorbent than any of the C8 aromatics. However, such diluents take up volume in the apparatus and are not necessary. Accordingly the stream, which is introduced into the apparatus through conduit 200, is preferably free of such diluent.

An extract stream is withdrawn from bed $A_n$ through conduit 202. The extract stream comprises a mixture of the purified para-xylene and the desorbent. As shown in FIG. 2, the withdrawal point of the extract stream though conduit 202 is between the point of introduction of the feed through conduit 207 and the point of introduction of the desorbent through conduit 200. A raffinate stream is withdrawn from bed $A_{n+j}$ through conduit 210. The raffinate stream comprises para-xylene-depleted C8 aromatics and desorbent.

In view of the configuration of the simulated moving bed process, the various feeds and products must share the conduits between the adsorbent beds and the rotary valve device (not shown). To prevent contamination of the extract stream with residual metaxylene, orthoxylene, and ethylbenzene from the residue of feed stream in the conduit, the conduit is flushed in two stages with first a primary medium and second with a secondary flush medium. Liquid, which is optionally withdrawn through conduit 201, may either be sent to the extract tower for recovery or recycled and used for primary flush through conduit 206 or secondary flush through conduit 204.

A first or primary flushing medium is introduced into conduit 206, including a terminal portion 214 of this conduit, which is connected to adsorbent apparatus 220. In FIG. 2, the primary flush fluid displaces residual feed in the conduit at the location of bed $A_{n+7}$, which is two beds above (i.e., two beds upstream, in terms of the direction of circulating bulk fluid) bed $A_{n+9}$ into which feed is introduced via conduit 207. Although not shown in FIG. 2, it will be understood that conduit 206 may be connected to beds located further away, e.g., bed $A_{n+6}$, or closer, e.g., bed $A_{n+8}$, than bed $A_{n+7}$. The primary flushing medium comprises at least two components, e.g., a non-C8 aromatic, such as desorbent and a C8 aromatics mixture, comprising, for example, from 80 to 95 volume percent para-xylene.

These components may be mixed upstream of a rotary valve device (not shown in FIG. 2) and passed together through the rotary valve device into conduit 206. In another embodiment, these components may be passed sequentially into conduit 206. For example, the C8 aromatics mixture, comprising from 80 to 95 volume percent para-xylene, may be passed first through a rotary valve device into conduit 206, followed by passing desorbent component through the rotary valve device and into conduit 206. In another embodiment, at least a portion of the C8 aromatics mixture, comprising from 80 to 95 volume percent para-xylene, may be passed directly to the terminal portion 214 of conduit 206 through conduit 209. A portion of the C8 aromatics mixture, comprising from 80 to 95 volume percent para-xylene, may also be introduced into a terminal portion 213 of conduit 207 via conduit 208 and introduced as feed to bed $A_{n+9}$. In another embodiment at least a portion of the C8 aromatics mixture, comprising from 80 to 95 volume percent para-xylene, may be combined with a different C8 aromatics mixture, comprising from 15 to 30 volume percent para-xylene, and this combined C8 aromatic mixture may be passed through a rotary valve device (not shown in FIG. 2) into conduit 207.

As shown in FIG. 2, a second or secondary flushing medium is introduced into conduit 203, including a terminal portion 204 of this conduit, which is connected to adsorbent apparatus 220. In FIG. 2, the secondary flush fluid displaces residual primary flush fluid in the conduit at the location of bed $A_{n+1}$, which is six beds above (i.e., six beds upstream, in terms of the direction of circulating bulk fluid) bed $A_{n+7}$ into which primary flush fluid is introduced and one bed below bed $A_n$ from which an extract stream is withdrawn via conduit 202. However, it will be understood that the flow of secondary flush fluid through conduit 203 may be diverted to a bed located further away from bed $A_n$ and closer to bed $A_{n+7}$. In FIG. 2, this diversion of flow is shown by conduit 205, which is connected to bed $A_{n+4}$.

When the secondary flush medium comprises little or no metaxylene, orthoxylene, and ethylbenzene, the secondary flush medium and the residue of primary flush medium in the conduit comprises little or no metaxylene, orthoxylene, and ethylbenzene, the secondary flush medium may flow towards a bed located close (e.g., one bed away) to the extract withdrawal point. When the secondary flushing medium and the residue of the primary flushing medium in the conduit are such that significant quantities of metaxylene, orthoxylene, and especially ethylbenzene are introduced, the bed, to which the secondary flushing medium is directed, the location of the secondary flush step should be further away from the extract point to allow sufficient separation of para-xylene from the other C8 aromatics.

Figure 3:
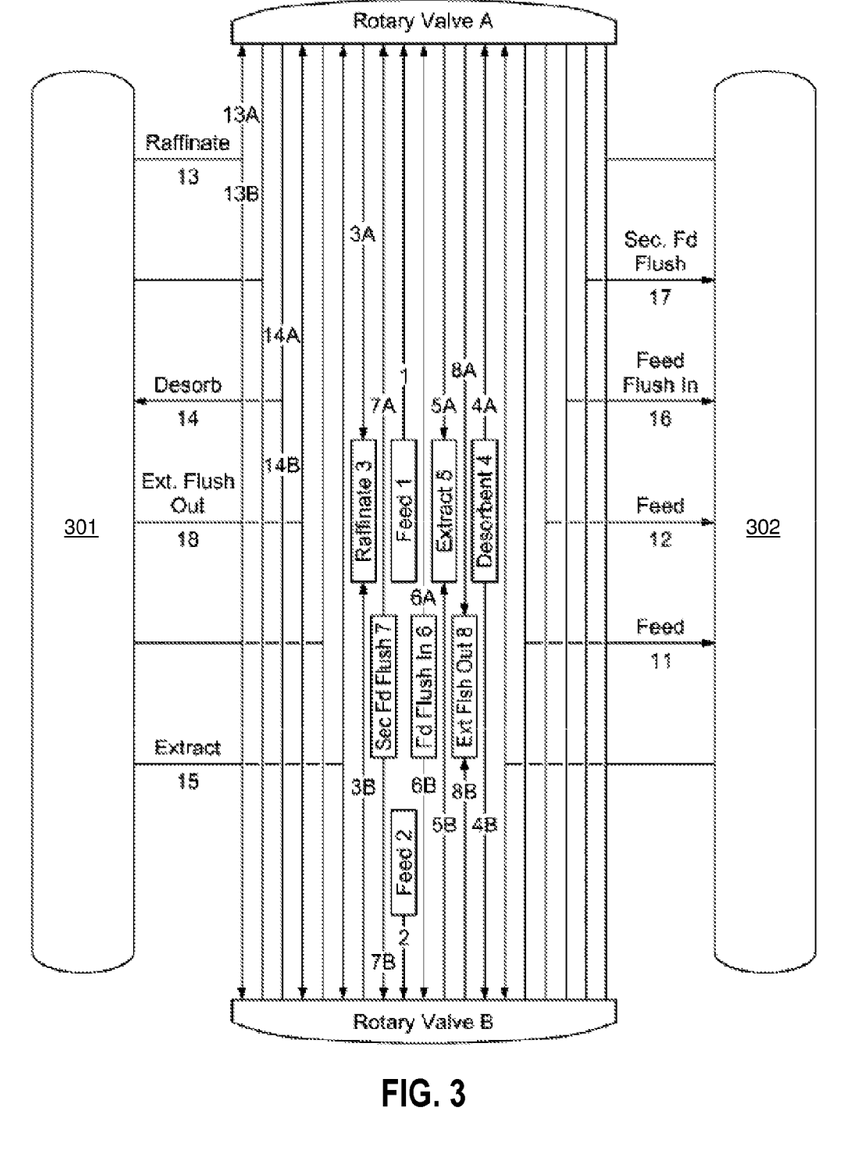
FIG. 3 is a schematic illustration of a simulated moving bed adsorptive separation system with dual rotary valves.

FIG. 3 depicts an embodiment in which dual parallel rotary valves are used. As shown in FIG. 3, the two feeds, preferably two different feeds, which in embodiments may be feeds selected from the group consisting of (i) an equilibrium mixture of xylenes; (ii) a mixture of xylenes from a selective process having an amount of p-xylene greater than an equilibrium concentration; and (iii) and a mixture of xylenes from a crystallization process having an amount of p-xylene less than an equilibrium concentration, are fed independently to each rotary valve A and B through lines 1 and 2, respectively. There is no loss of feed flushing capability, since the second rotary valve B is configured (plumbed) differently from the first rotary valve A with respect to the bed lines. Throughout the several views the internal plumbing of the rotary valves is not shown because it is conventional per se with respect to each rotary valve. Parallel rotary valves A and B are configured independently to allow optimization of more than one feed. As depicted in the diagram, the three product streams (Raffinate 13, Extract 15 and Extract Flush Out 18) are withdrawn from the same location (sieve chamber 101).

The respective streams of Raffinate, Extract, and extract Flush Out (bed lines 13, 15, and 18) split (e.g., into 13A and 13B; other notations omitted on the figure for convenience of view) and flow through each rotary valve A and B before recombining (streams 3A, 3B; 5A, 5B; 8A and 8B; respectively), at the outlets, respectively, for each stream. The plumbing for the outlets to processing downstream, such as by distillation, recycle, and the like, as discussed elsewhere herein, are not shown in the figure for convenience of view but are per se conventional plumbing. Feed streams 4 (Desorbent), 6 (Feed Flush in) and 7 (Secondary Feed Flush) split equally (4A, 4B; 6A, 6B; 7A and 7B) through each rotary valve A and B and then recombine (streams 14A and 14B combine into 14); likewise the appropriate streams combine (other notations omitted for convenience of view) into streams 16 and 17 before entering the sieve chambers 101 and 102 as shown in FIG. 1.

In the prior art, normally a single feed stream, which is a blend of two or more streams, is also split equally through each rotary valve and recombined to a single feed location in the sieve chambers. However, mixing of feedstreams having different concentrations is, generally, thermodynamically inefficient. Employing parallel rotary valves allows disparated feed streams (feed 1 and feed 2) to be fed individually from each rotary valve by streams 11 and 12 to one or both sieve chambers (illustrated in the embodiment of FIG. 3 by the single sieve chamber 102). As with a distillation tower, the optimum location of a given feed is a function of composition and may be determined by one skilled in the art.

There are numerous other embodiments of the parallel rotary valve apparatus that will immediately become apparent to one of ordinary skill in the art, such as those described in U.S. Pat. No. 8,168,845, which is incorporated by reference in its entirety.

Again, it should be emphasized, as would be known by one of skill in the art, that the positions described herein for the feed, flush and desorbent inputs and extract and raffinate outputs are relative and that, although the actual positions change by virtue of the movement of the rotary valve or valves, the relative positions of the conduits remains the same. Thus, it will be understood by one of ordinary skill in the art that FIGS. 2 and 3 depict simplified simulated moving bed apparatuses with a rotary valve or parallel rotary valves, wherein countercurrent "movement" of the solids in absorbent beds relative to the fluid streams is simulated by the use of the rotary valve or valves (not shown in FIG. 2). As the valve or valves rotate, the zones previously discussed move through the column in a stepwise sequence due to the change in the stream flows through the valve.

Figure 4:
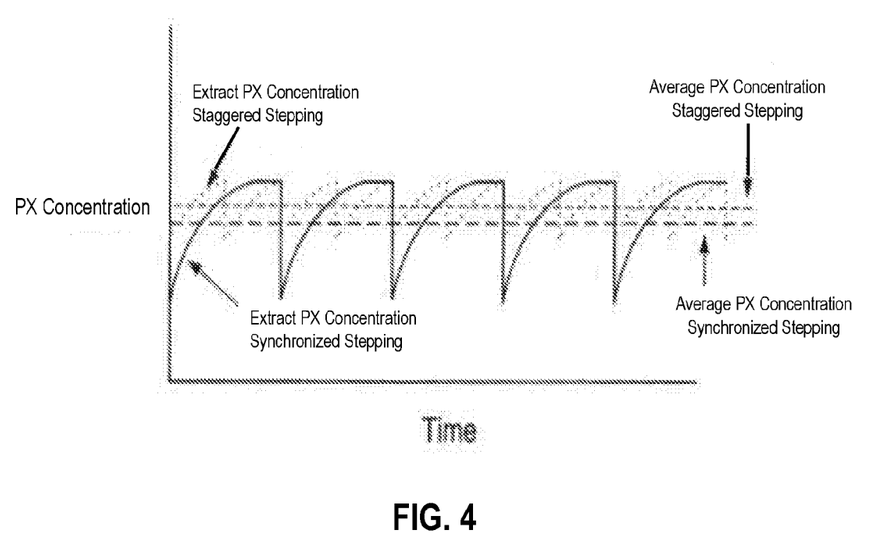
FIG. 4 is a graphical representation of the para-xylene concentration of the extract stream when synchronized and staggered stepping is used.

While the rotary valve(s) provides an effective method of directing the various feeds and flushes in a simulated moving bed process, there is an inherent inefficiency in the process due to the stepping of the rotary valve(s). Each time the rotary valve(s) steps, the extract withdrawal point jumps forward in the composition profile. Referring to the composition profile in FIG. 1, the shaded band encompassing the extract point 103 represents the withdrawal area of the profile. Within this withdrawal area, the para-xylene concentration increases throughout the step. The concentration of para-xylene during the step can vary up to 15 to 25% of the average para-xylene concentration of the extract. Once the rotary valve(s) steps, the para-xylene concentration of the extract drops immediately and gradually increases until the next step of the rotary valve(s). This "sawtooth" variation of para-xylene concentration in the extract, shown by the solid line labeled as "Extract PX Concentration Synchronized Stepping" in FIG. 4, results in a lower composite para-xylene concentration, shown as the bolded dashed line labeled as "Average PX Concentration Synchronized Stepping," and hence lower separation efficiency. Additionally, when the rotary valve(s) steps, the amount of contaminants in the extract increases immediately and decreases throughout the step.

The net composite para-xylene concentration of the extract may be improved by staggering the step times of the dual rotary valves. Thus, the rotary valves do not step simultaneously, but the second rotary valve steps at a time different from the first rotary valve. In other words, the second rotary valve steps at a point during the step time of the first rotary valve. The time differential between when the first rotary valve steps and when the second rotary valve steps may be equal to or different than the time differential between when the second rotary valve steps and when the first rotary valve steps. In one embodiment, the first rotary valve, rotary valve A in FIG. 3, steps every 50 to 120 seconds and the second rotary valve, rotary valve B in FIG. 3, which also steps every 50 to 120 seconds, steps about halfway through the step time of the first rotary valve. For example, if rotary valve A stepped every 90 seconds, rotary valve B would step about 45 seconds after rotary valve A. In a different embodiment, rotary valve B steps earlier than the midpoint of the step time of rotary valve A. For example, rotary valve B could step about 30 seconds after rotary valve A and rotary valve A steps about 60 seconds after rotary valve B.

The time differential between the steps of the first and second rotary valves may be manipulated by one skilled in the art to maximize the para-xylene concentration in the extract, but in a preferred embodiment, the second rotary valve steps within about 10 seconds of the midpoint of the step time of the first rotary valve. In embodiments, the midpoint of the step time takes into account that the first 5 to 15 seconds of the extract withdrawal consist primarily of the secondary flush material that remains in the line from the secondary flush. Thus, the midpoint of the step time would be found by subtracting 5 to 15 seconds from the overall step time and dividing by two.

In embodiments, the staggering times differ for each step throughout the valve cycle. One embodiment utilizes different staggering times for the upper beds to overcome the profile disturbance from the circulation piping.

Although staggering the steps of the dual rotary valves doubles the number of jumps in paraxylene concentration in the extract, the magnitude of the concentration dips is decreased by about half, increasing the net composite para-xylene concentration. The para-xylene concentration of the extract when the stepping of the dual rotary valves are staggered is shown by the dotted line labeled "Extract PX Concentration Staggered Stepping" in FIG. 4, and the resulting improvement in the net composite para-xylene concentration is shown by the dashed line labeled "Average PX Concentration Staggered Stepping." Additionally, the magnitude of the contaminant concentration increases after a step will be much less than half, resulting in less average contaminants in the extract.

Similar composition changes occur for the raffinate composition. Although, it is recognized the changes in recovery likely represent less opportunity from a process optimization viewpoint, this idea can be similarly applied to reduce recovery loss or more importantly increase unit throughput within the supplied equipment.

Staggered stepping also improves the process control since the magnitude of the changes in recirculation flow is lessened. This in turn minimizes the magnitude of pressure spikes related to the amount of flow through the pipes in the process, which reduces damage to the adsorbent that can occur with pressure spikes and large changes to recirculation flow over time. Thus, the separation efficiency of the simulated moving bed process is improved, allowing for increased capacity and/or reduced energy consumption.

The rotary valves may be operated at identical flow rates or substantially different flow rates. For example, one rotary valve could be operated at a reduced rate, such as 34% of the total flow, and the second rotary valve could operate at 66% of the total flow. Utilizing differing flow rates for the dual rotary valves could be especially advantageous in cases where feeds with different composition are available, such as feeds enriched in para-xylene or depleted in ethylbenzene. Operating the dual rotary valves at differing flow rates can also reduce the increase in contaminant concentration of the extract after a step.

Similar composition changes occur for the composition of the raffinate stream. Although the changes in recovery of the raffinate components likely represent less opportunity from a process optimization viewpoint, staggering of valve step times can be similarly applied to reduce recovery loss, or more importantly, increase unit throughput within the supplied equipment.

Additional Embodiments

Embodiment 1. A simulated moving bed process for separating para-xylene using at least a first rotary valve and a second rotary valve fluidly connected to each other and to plural adsorptive separation chambers, wherein each of said rotary valves direct the input of at least one multicomponent feed, at least one flushing medium, and at least one desorbent into, and the output of at least one raffinate and at least one extract from the adsorptive separation chambers, the improvement comprising staggering the step times of the first rotary valve and a second rotary valve based on a predetermined time differential between the steps.

Embodiment 2. The process of Embodiment 1, wherein the time differential between the first rotary valve step and the second rotary valve step equals the time differential between the second rotary valve step and the first rotary valve step.

Embodiment 3. The process of Embodiment 1, wherein the time differential between the first rotary valve step and the second rotary valve step is different than the time differential between the second rotary valve step and the first rotary valve step.

Embodiment 4. The process of Embodiments 1 or 3, wherein the second rotary valve steps within about 10 seconds of the midpoint of the step time of the first rotary valve.

Embodiment 5. The process of Embodiments 1, 3 or 4, wherein the predetermined time differential varies between the plural adsorptive chambers.

Embodiment 6. The process of any one of Embodiments 1-5, wherein the first rotary valve is operated at a different flow rate than the second rotary valve.

Embodiment 7. The process of any one of Embodiments 1-6, wherein the at least one multicomponent feed is selected from an equilibrium mixture of xylenes, an enhanced para-xylene stream from a toluene disproportionation unit, an enhanced para-xylene stream from a toluene methylation unit, and filtrate from a crystallizer which is low in para-xylene.

Embodiment 8. A process for separating para-xylene in a simulated moving bed system comprising the steps of: (a) introducing at least one multicomponent feed comprising at least one desired product through at least one conduit into a simulated moving bed adsorption apparatus comprising a first rotary valve and a second rotary valve in fluid communication with the at least one conduit and plural adsorptive separation chambers; (b) after a predetermined step time, advancing the first rotary valve and a second rotary valve and flushing the at least one conduit in step (a) with at least one initial flushing medium to flush residue of said first multicomponent feed from the at least one conduit in step (a) into the apparatus; (c) after a predetermined step time, advancing the first rotary valve and a second rotary valve and flushing the at least one conduit with a second flushing medium to flush residue of the initial flushing medium from the at least one conduit in step (a) into the apparatus; (d) after a predetermined step time, advancing the first rotary valve and a second rotary valve and withdrawing an extract stream through the at least one conduit from the apparatus through the at least one conduit; and (e) after a predetermined step time, advancing the first rotary valve and a second rotary valve and passing a desorbent through the at least one conduit into the apparatus; wherein the predetermined step times for the first rotary valve and a second rotary valve are staggered.

Embodiment 9. The process of Embodiment 8, wherein the predetermined step time of the second rotary valve is about halfway through the predetermined step time of the first rotary valve.

Embodiment 10. The process of Embodiment 8, wherein the predetermined step time of the second rotary valve is less than the predetermined step time of the first rotary valve.

Embodiment 11. The process of Embodiment 8 or 10, wherein the second rotary valve steps within about 10 seconds of the midpoint of the step time of the first rotary valve.

Embodiment 12. The process of Embodiment 8, 10 or 11, wherein the predetermined step time varies between the plural adsorptive separation chambers.

Embodiment 13. The process of any one of Embodiments 8-12, wherein the first rotary valve is operated at a different flow rate than the second rotary valve.

Embodiment 14. The process of any one of Embodiments 8-13, wherein the at least one multicomponent feed is selected from an equilibrium mixture of xylenes, an enhanced para-xylene stream from a toluene disproportionation unit, an enhanced para-xylene stream from a toluene methylation unit, and filtrate from a crystallizer which is low in para-xylene.

Embodiment 15. An apparatus for the continuous simulated countercurrent adsorptive separation of para-xylene comprising plural adsorptive separation chambers fluidly connected with plural bedlines $A_1$ through $A_{n+j}$, wherein n>2 and n+j is the total number of bedlines, which in turn are fluidly connected with a matrix of conduits to distribute plural input streams, including desorbent, a primary flush input and a secondary flush input, and at least two multicomponent feeds differing in the concentration of para-xylene, to said plural bedlines, and plural output streams, including a primary flush output and a secondary flush output, an extract comprising a para-xylene-enriched product, and raffinate, from said plural adsorptive separation chambers, wherein the plural input streams and plural output streams are distributed by a first and second rotary valve in fluid communication with the conduits, the improvement comprising staggering the step time of the first rotary valve from the step time of the second rotary valve.

Embodiment 16. The apparatus of Embodiment 15, wherein the second rotary valve steps about halfway through the step time of the first rotary valve.

Embodiment 17. The apparatus of Embodiment 15, wherein the second rotary valve steps prior to about halfway through the step time of the first rotary valve.

Embodiment 18. The apparatus of Embodiment 15 or 17, wherein the second rotary valve steps within about 10 seconds of the midpoint of the step time of the first rotary valve.

Embodiment 19. The apparatus of Embodiment 15, 17 or 18, wherein the step time varies between the plural adsorptive separation chambers.

Embodiment 20. The apparatus of any one of Embodiments 15-19, wherein the first rotary valve is operated at a different flow rate than the second rotary valve.

Embodiment 21. The apparatus of any one of Embodiments 15-20, wherein the at least two multicomponent feeds are selected from an equilibrium mixture of xylenes, an enhanced para-xylene stream from a toluene disproportionation unit, an enhanced para-xylene stream from a toluene methylation unit, and filtrate from a crystallizer which is low in para-xylene.

The invention has been described above with reference to specific details and embodiments which, it will be understood by one of ordinary skill in the art, are intended to be exemplary and not limiting. Accordingly, the invention can be practiced other than as specifically set forth herein.

Trade names, where used, are indicated by a ™ symbol or ® symbol, indicating that the names may be protected by certain trademark rights, e.g., they may be registered trademarks in various jurisdictions. All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. When numerical lower limits and numerical upper limits are listed herein, ranges from any lower limit to any upper limit are contemplated. While the illustrative embodiments of the invention have been described with particularity, it will be understood that various other modifications will be apparent to and can be readily made by those skilled in the art without departing from the spirit and scope of the invention.

What is claimed is:

1. An apparatus for the continuous simulated countercurrent adsorptive separation of para-xylene comprising plural adsorptive separation chambers fluidly connected with plural bedlines $A_1$ through $A_{n+j}$, wherein n>2 and n+j is the total number of bedlines, which in turn are fluidly connected with a matrix of conduits to distribute plural input streams, including desorbent, a primary flush input and a secondary flush input, and at least two multicomponent feeds differing in the concentration of para-xylene, to said plural bedlines, and plural output streams, including a primary flush output and a secondary flush output, an extract comprising a para-xylene-enriched product, and raffinate, from said plural adsorptive separation chambers, wherein the plural input streams and plural output streams are distributed by a first and second rotary valve in fluid communication with the conduits, the improvement comprising staggering the step time of the first rotary valve from the step time of the second rotary valve.

2. The apparatus of claim 1, wherein the second rotary valve steps about halfway through the step time of the first rotary valve.

3. The apparatus of claim 1, wherein the second rotary valve steps prior to about halfway through the step time of the first rotary valve.

4. The apparatus of claim 1, wherein the second rotary valve steps within about 10 seconds of the midpoint of the step time of the first rotary valve.

5. The apparatus of claim 1, wherein the step time varies between the plural adsorptive separation chambers.

6. The apparatus of claim 1, wherein the first rotary valve is operated at a different flow rate than the second rotary valve.

7. The apparatus of claim 1, wherein the at least two multicomponent feeds are selected from an equilibrium mixture of xylenes, an enhanced para-xylene stream from a toluene disproportionation unit, an enhanced para-xylene stream from a toluene methylation unit, and filtrate from a crystallizer which is low in para-xylene.

* * * * *